United States Patent [19]

Jasper

[11] Patent Number: 4,708,646
[45] Date of Patent: Nov. 24, 1987

[54] ORTHODONTIC DEVICE FOR CORRECTING THE BITE

[76] Inventor: James J. Jasper, P.O. Box 1540, Guerneville, Calif. 95446

[21] Appl. No.: 846,809

[22] Filed: Apr. 1, 1986

[51] Int. Cl.$^4$ ............................................. A61C 3/00
[52] U.S. Cl. ........................................ 433/19; 433/22
[58] Field of Search ................. 433/18, 19, 21, 22, 433/23, 24, 5, 6

[56] References Cited

U.S. PATENT DOCUMENTS

| | | | |
|---|---|---|---|
| 741,687 | 10/1903 | MacDowell | 433/5 |
| 3,121,953 | 2/1964 | Asher | 433/5 |
| 3,137,941 | 6/1964 | Andrews | 433/5 |
| 3,315,359 | 4/1967 | Moss | 433/5 |
| 3,618,214 | 11/1971 | Armstrong | 433/19 |
| 3,997,970 | 12/1976 | Hodgson | 433/19 |
| 4,439,149 | 3/1984 | DeVincenzo | 433/6 |
| 4,462,800 | 7/1984 | Jones | 433/19 |

Primary Examiner—Gene Mancene
Assistant Examiner—Adriene J. Lepiane
Attorney, Agent, or Firm—Owen, Wickersham & Erickson

[57] ABSTRACT

An orthodontic appliance for correcting an overbite or underbite condition is disclosed. The appliance comprises one or a pair of flexible members which are attached at opposite ends to the upper and lower jaws of a patient. The end attachments allow the members to swivel freely and the members to bend when the patient is chewing, talking or cleaning his or her teeth, but when the patient is relaxed, the appliance members tend to straighten and apply a small but continuous force generally along the normal growth direction for a human jaw to overcome the abnormality being treated.

20 Claims, 13 Drawing Figures

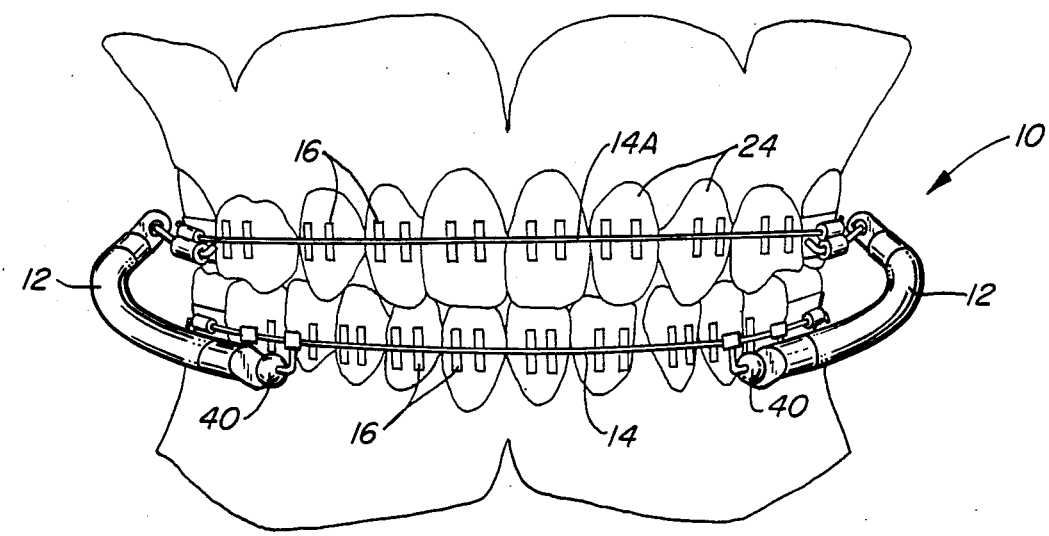
FIG._1.
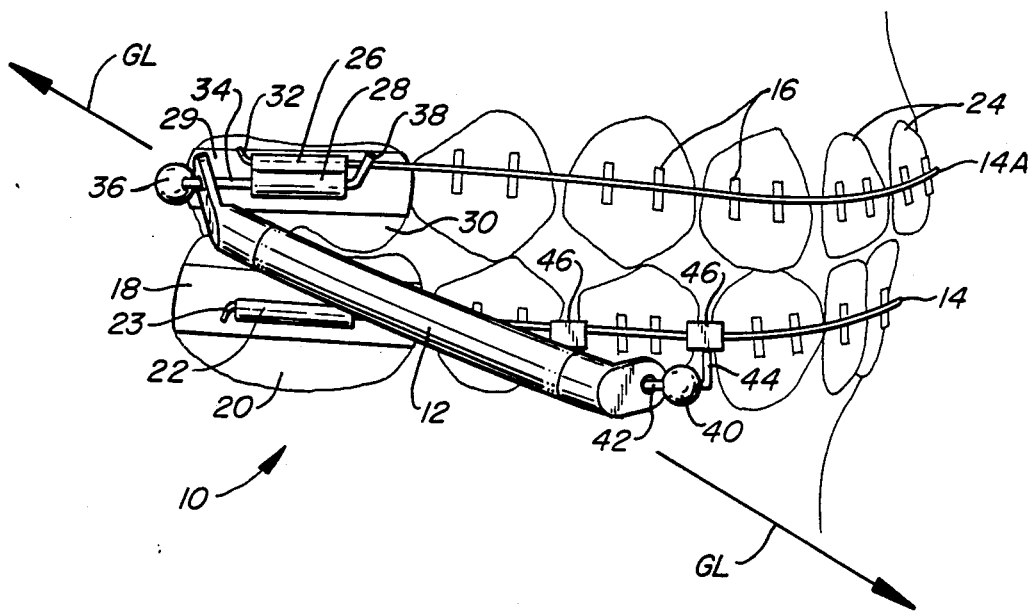
FIG._2.

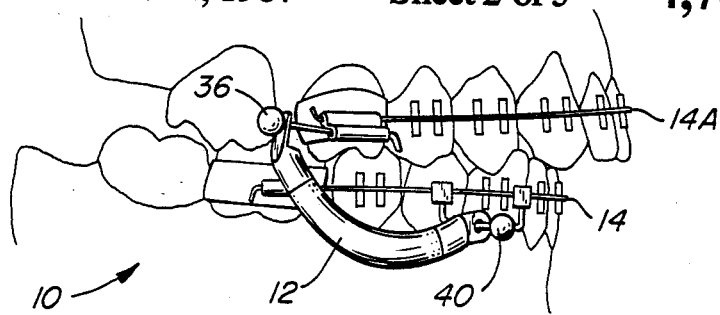
FIG._3A.
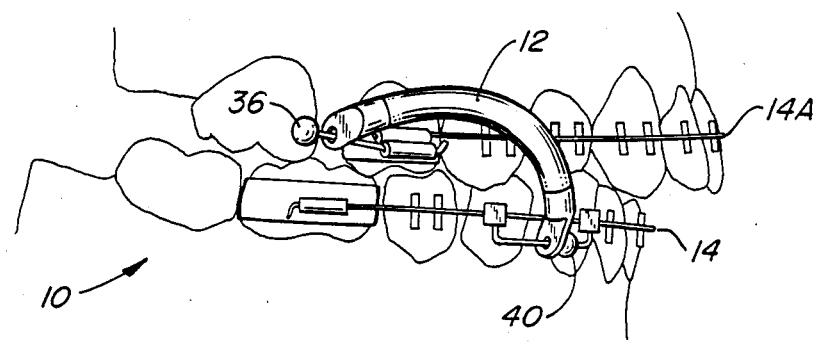
FIG._3B.
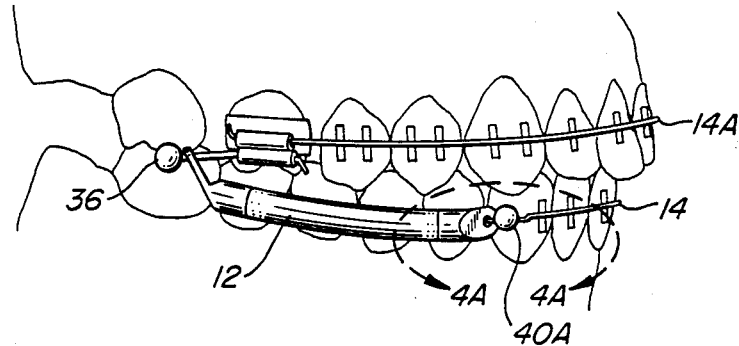
FIG._4.
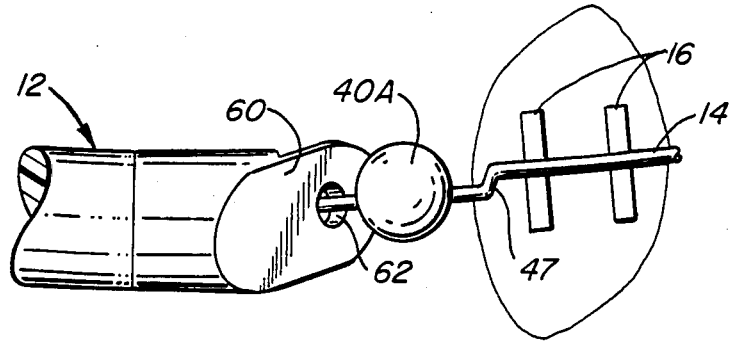
FIG._4A.

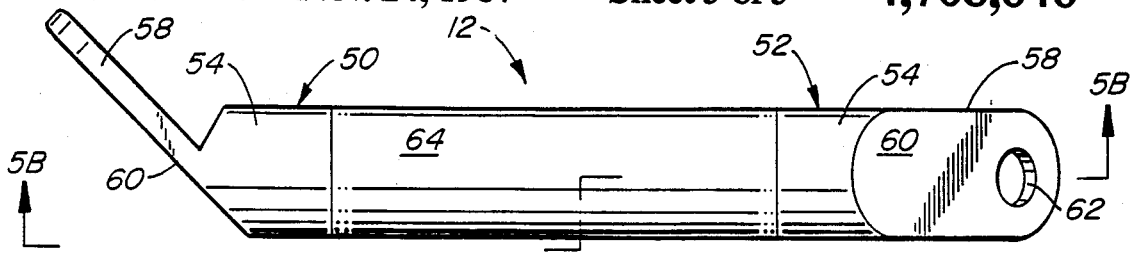
FIG._5A.
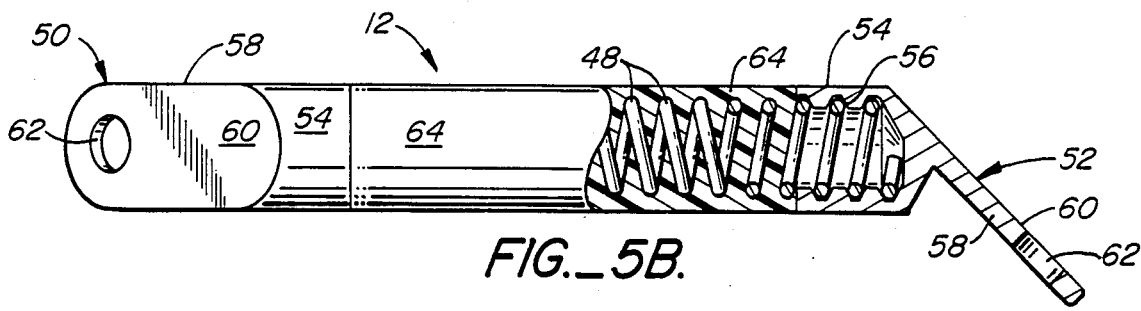
FIG._5B.
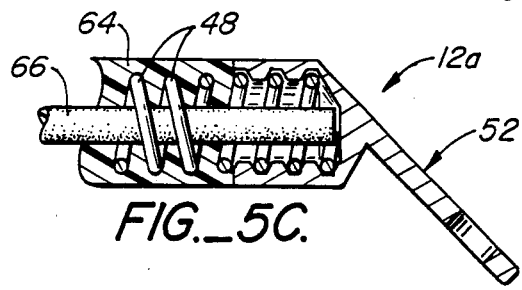
FIG._5C.
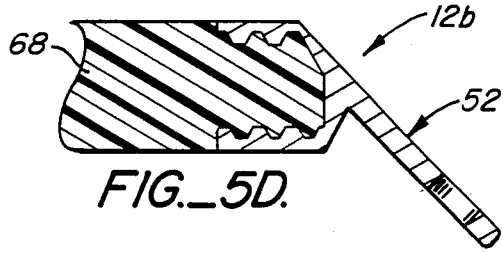
FIG._5D.
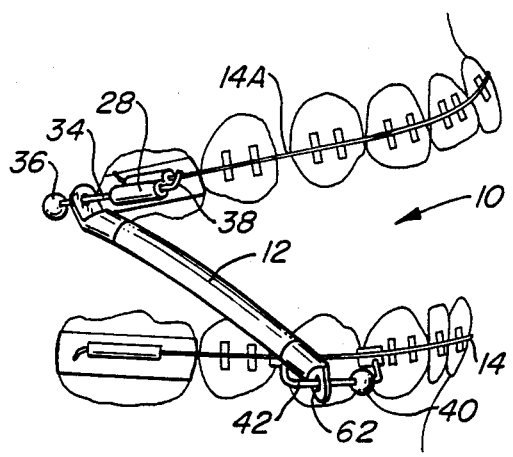
FIG._6.
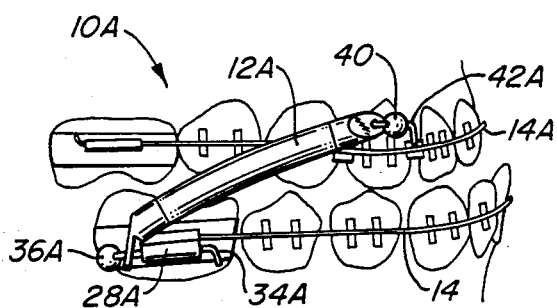
FIG._7.
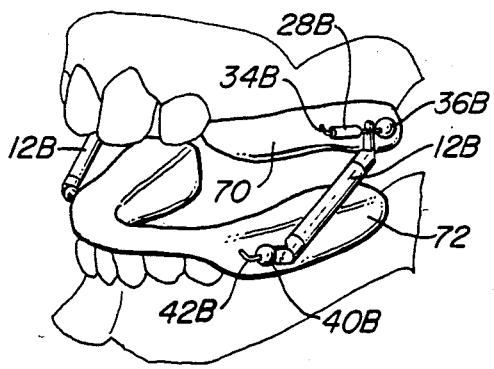
FIG._8.

ORTHODONTIC DEVICE FOR CORRECTING THE BITE

This invention relates to orthodontic appliances and more particularly to a device for treating malocclusion of the upper and lower jaws of a patient commonly known as overbite or underbite.

BACKGROUND OF THE INVENTION

When a person's jaws, teeth, or facial muscles do not develop normally, various type misfits or malocclusions occur between the upper and lower jaws and/or the individual teeth of the upper and lower arches of teeth. Three common types of malocclusions as categorized by orthodontists are described as follows: Class I—The jaw relation is normal but individual teeth in the upper or lower arch are not growing in ways to achieve a good fit with their corresponding teeth in the opposite arch. This malocclusion of the teeth is commonly corrected by the installation of braces to move or straighten the misdirected teeth; Class II—Wherein the lower jaw is not growing downward and forward in a normal manner along an imaginary sloping line from the ear to the person's lower jaw which has been called the Y axis of growth by orthodontists. In such cases, the upper and lower arches of teeth do not fit properly, and the fit or bite of the teeth occurs between the wrong teeth in the upper and lower arch. This condition, called an overbite, is commonly corrected by moving the lower jaw forward by some means so that the proper teeth of the upper and lower arch meet each other when the jaws are closed or by moving the upper jaw back. Treatment requires that the jaw be held in the new proper bite position so that the jawbones and muscles will grow in ways which support this new bite; Class III—Wherein the lower jaw has grown forward so far that when the mouth is closed, the upper arch of teeth sets down behind the lower arch of teeth. This condition is called underbite and is commonly corrected either with the use of braces with rubber bands or by surgery wherein portions of the rear lower jaw are removed and re-aligned so that the upper arch of teeth sit properly ahead of the lower arch when the jaws were closed. A complication of underbite or Class III type problems is that since the lower jaw has in a sense gotten ahead of the upper jaw, the growth of the lower jaw does not push forward the growth of the upper jaw and the facial muscles are not properly developed. If left untreated, the condition worsens as the lower jaw protrudes further and the upper jaw and its muscles remain undeveloped. This condition creates a sunken facial profile.

Orthodontists have previously used several types of appliances to correct each of the three major classes of orthodontic problems.

Braces are generally appliances for the correction of many types of orthodontic problems, particularly Class I problems. However, they have no direct effect on the bite problems of Class II or Class III patients. To correct the bite, one must put pressure on or link together the entire arch of teeth or the jaws of the patient. As the braces are normally in place to correct tooth alignment problems, they provide a convenient point of attachment for a myriad of bite correcting appliances from head gears to rubber bands.

Ideally, the patient may use braces and a bite correcting device at the same time. In this way, the entire malocclusion of teeth and jaws can be simultaneously corrected. Some appliances preclude the use of braces and require two separate phases of treatment, one to correct the alignment of the jaws and one to correct the alignment and fit of the teeth. The problem with orthodontic appliances heretofore used was that almost all of them were removable by the patient and thus were ineffective or unpredictable in treatment results.

One type of orthodontic appliance used with braces and generally termed elastics or rubber bands, has been used to treat Class I, Class II, and Class III problems. Such appliances come in different sizes and strengths and are used to create a pull-type pressure between two points in the patient's mouth. They are usually attached to normal braces and are used intermaxillary (between two jaws) and intramaxillary (same jaw) as required, having the advantages of being removable for chewing and brushing and also being disposable and therefore easily replaced rather than cleaned. In use, they exert only light forces in the two to eight ounce range, thereby not damaging braces.

However, a serious disadvantage with elastics is that they are removable by the patient, who often forgets to replace them after eating. This greatly reduces the effectiveness of the treatment which is dependent on consistent application and thus the cooperation of the patient. When the patient fails to keep the elastics properly attached, the treatment is not only retarded but in some instances other pressures set on braces can undo the gains made when the elastics were attached. An additional disadvantage is that the elastics stretch and weaken after use and thus fail to provide a steady or consistent amount of force during the period of use. Finally, the force exerted by elastics is a pull-type force which creates a straight line of tension between two points. Thus, when elastics are attached between the upper and lower jaw to treat an overbite condition, they pull the jaws together at an angle which is almost perpendicular to the natural angle of growth along the Y axis. This indirect use of force to encourage the lower jaw to grow forward and downward in Class II type problems requires much more time than a more direct use of force to push the lower jaw forward along the Y axis.

Several attempts have been made to replace elastics with small springs which pull the jaws together, as for example in the patent to Armstrong U.S. Pat. No. 3,618,214 which uses springs inside plastic tubes. This device operates in the pull mode like an elastic. However, it offers none of the advantages of the elastic and suffers from all the disadvantages plus the additional disadvantage of being obviously uncomfortable for the patient. Another attempt to solve the overbite problem with an elastic type device is disclosed in the patent to Nelson U.S. Pat. No. 4,074,433 which utilizes a pull cable retained by spring loaded anchor elements. However, this device not only has the inherent limitations of conventional elastics but would obviously be more difficult to install, adjust, and keep clean.

Functional appliances have also been used to treat bite problems. These utilize molded pieces of plastic and wire which work something like the mouth piece used by boxers. In place, such an appliance exerts light forces in the mouth in the very low range of zero to ¼ ounce and can achieve favorable results when used consistently by the patient. However, a serious disadvantage with such devices is that they are removable, easily taken out, often lost and easily broken. Also, a patient cannot use the mouth to eat or brush while such molded devices are in normal position. Therefore functional appliances have proven to be generally unpredictable in treating an bite problems because most patients find them too inconvenient for regular use and cosmetically unpleasant.

Still another appliance which has been used to counteract and overcome an overbite condition is a headband which is attached to the braces. Rather than pushing the lower jaw forward, it works by pulling the upper jaw back. To do this, such appliances use one to two pounds of force, which is the maximum which can be tolerated by braces. The head gears have the same advantages and disadvantages as the functional appliances. They are obviously cosmetically undesirable.

In the early 1900's a Dr. Herbst, in Germany, developed an appliance which pressured the lower jaw forward to accelerate its growth in order to treat an overbite condition. This was the first fixed or non-removable bite correcting appliance. The Herbst device used rigid steel bars or rods which, once installed, could not be removed by the patient. However, the normal biting force exerted by the jaws of a patient and transmitted by the rigid bars required the placement of a heavy metal reinforced plastic overlay over the upper and lower teeth or the placement of steel crowns on the teeth. The rigid bars and the overlay support made eating extremely difficult for a patient and created severe oral hygiene problems as well as cosmetic problems. Moreover, the rigidity and lack of flexible connections for the Herbst links transmitted such large force components (18-30 lbs.) that damage to the appliance or braces thereon often resulted.

Despite the aforesaid drawbacks and problems, Herbst and Herbst-like appliances have been used, as shown by the patents to Northcutt U.S. Pat. No. 3,798,773 and Mason U.S. Pat. No. 4,551,095. In both Northcutt and Mason, the rigid steel bar links attached to an associated heavy metal reinforced plastic overlay are replaced by a system of rigid telescoped tubes attached to the arch wires of braces. These appliances are attached to the arch wire of braces by relatively complicated connecting devices that allow for limited movement. Thus, the rigid bar links, as with earlier Herbst devices, not only tend to exert excessive forces at their attachment points but also cannot be moved aside by the patient for chewing, speaking, and hygiene.

It is therefore a general object of the present invention to provide an improved orthodontic appliance for treating patients with an overbite or underbite malocclusion that overcomes the aforesaid problems of prior art devices.

Another object of the invention it to provide an orthodontic appliance for treating an overbite condition that can be worn constantly during a prolonged treatment period and will bend upwardly or downwardly when necessary to allow the patient to talk, chew and maintain proper oral hygiene with the appliance installed.

Another object of the invention is to provide an orthodontic appliance for correcting an overbite condition that is relatively easy to install in a patient's mouth and also relatively easy to adjust so that a proper amount of push force will be applied to make the treatment effective.

Another object of the invention is to provide an orthodontic appliance for treating an overbite condition that has a degree of flexibility and movement and thereby eliminates the problem of creating excessive stresses at attachment points within the patient's mouth.

Yet another object of the invention is to provide an orthodontic appliance that can be installed and used with equal effectiveness whether or not the patient is wearing braces.

Still another object of the invention is to provide an orthodontic appliance that is cosmetically acceptable because it requires no external component outside the mouth that can be seen.

SUMMARY OF THE INVENTION

The orthodontic appliance according to the present invention functions to apply a force within a patient's mouth that pushes the lower jaw of a patient having an overbite condition forward from the upper jaw generally along his or her normal growth axis. The appliance is constructed so that it has a degree of flexibility and also end attachment means which enables it to turn or swivel adjacent its anchor points on the upper and lower jaws of the patient. Thus, a patient can wear a pair of appliances with a minimum of discomfort while retaining the ability to talk, chew food and perform normal oral hygiene procedures such as tooth brushing when necessary.

Each appliance, according to the invention, comprises an elongated, generally cylindrical and somewhat flexible device having fixed end caps, each with an attachment flange that extends at an angle to the axial centerline of the elongated device. An opening is provided in each attachment flange. For an installation in a patient to treat an overbite condition, one attachment flange is connected to a rearward or distal anchor located distally on the upper jaw near the patient's upper molars. The other attachment flange of the device is retained by a forward or mesial anchor located on the patient's lower jaw near the lower bicuspid teeth. The mesial anchor may be a structural stop member such as a small metal ball fixed to a suitable wire such as an arch wire or an extension thereon attached to normal braces on the patient's teeth. The distal anchor may also be a small ball fixed to an adjustable rear wire that is retained within the molar tube attached to the patient's upper jaw teeth. The length of the rear wire and thus the position of the distal anchor can be adjusted so that each appliance is essentially straight and exerts a small axial force against the patient's lower jaw to hold the jaw in the normal bite position. Since this corrective force is exerted along the normal growth line of the jaw during a high percentage of the time that it is worn, and a pair of appliances can normally be worn constantly without discomfort, they are highly effective in correcting the overbite condition within a relatively short period as opposed to prior techniques. Variations in anchoring means can be provided within the scope of the invention to accommodate patients with or without braces and in either case, the appliances can be installed quickly and easily adjusted by a skilled orthodontist.

Other objects, advantages and features of the invention will become apparent from the following detailed description presented in conjunction with the accompanying drawing.

BRIEF DESCRIPTION OF THE DRAWING

FIG. 1 is a frontal view of an orthodontic appliance according to the present invention as it appears when installed in a patient's mouth.

FIG. 2 is a side view of the orthodontic appliance shown in FIG. 1.

FIG. 3A is a side view of the appliance of FIG. 1 shown with the patient's jaws in an overbite position and with the appliance swiveled and flexed in a downward manner.

FIG. 3B is another side view of the appliance of FIG. 1 similar to FIG. 3A but with the appliance swiveled and flexed in an upward manner when the patient's jaws are in an overbite position.

FIG. 4 is a side view showing one side of a patient's open mouth having installed therein a modified form of appliance embodying principles of the present invention.

FIG. 4A is an enlarged fragmentary view of one end attachment for the appliance of FIG. 4 and taken at line 4A—4A thereof.

FIG. 5A is an enlarged view in elevation of the appliance element according to the present invention.

FIG. 5B is a view in section taken along the line 5B—5B of FIG. 5A showing internal components of the appliance element.

FIG. 5C is a fragmentary view in section of a modified form of appliance element.

FIG. 5D is a fragmentary view in section of another modified form of appliance element.

FIG. 6 is another side view of an appliance of FIG. 1 as it appears when the patient's mouth is open.

FIG. 7 is a side view of an appliance according to the present invention as shown when installed in a patient's mouth to correct an underbite condition or a Class III problem.

FIG. 8 is a view in perspective showing an orthodontic device according to the invention as it appears when installed on a patient not wearing teeth-straightening braces.

DETAILED DESCRIPTION OF EMBODIMENT

With reference to the drawing, FIGS. 1 and 2 show a front and side view respectively of the mouth of an orthodontic patient within which is installed an appliance 10 embodying the principles of the present invention. In broad terms, the appliance comprises a pair of elongated, somewhat flexible members 12 which are installed on opposite sides of the patient's mouth. Each member 12 is constructed so that it can be attached to anchor means on the upper jaw and lower jaw yet be able to swivel about such anchor means. Although each member is itself flexible to a degree, it tends to maintain a normal straight configuration with its axis in a straight line. When in this straight configuration, each member is relaxed and is transmitting very light forces. When bent by the patient as they retrude into their improper bite, the inherent reactive internal forces within each member 12 tend to counteract the external force and thereby return the member to its straight configuration and push in the 2-20 ounce force range. Thus, when installed, as shown in FIG. 2, each member 12 of the appliance 10 will exert a small but effective force coincident with the patient's normal growth line (designated GL) to push the lower jaw outwardly relative to the upper jaw and thereby counteract and correct an overbite condition.

When it becomes necessary for the patient to move the lower jaw in order to talk, to chew food or to clean his teeth, the appliance members 12 will flex or bend and also swivel at their ends, as shown in FIGS. 3A and 3B. In FIG. 3A, the appliance member 12 is shown pivoted downwardly and outwardly from gum of the lower jaw, as, for example, when the patient is chewing. In FIG. 3B, the same appliance member is shown pivoted upwardly in an alternate position that may be conveniently utilized when the patient is either chewing or cleaning his teeth. Yet, when the patient is relaxed and particularly when asleep, the appliance member will again straighten out and push the lower jaw outwardly into the normal bite position, as shown in FIG. 2.

In the embodiment shown in FIGS. 1-3B, appliance 10 is shown installed on a patient wearing orthodontic braces, since it is more often the case that an orthodontic patient will simultaneously undergo treatment for teeth straightening and positioning while also being treated for an overbite condition. As shown, standard orthodontic braces comprise an arch wire 14 which is attached to mounting brackets 16 that are temporarily bonded to the patient's teeth. Normally, the ends of each arch wire on the lower jaw are retained by a suitable means such as a band 18 that is anchored to a molar 20 on each side. In the embodiment shown (see FIG. 3A), the end of the arch wire 14 on the lower jaw extends through a tube 22 and is bent to one side at the outer end 23 thereof to hold it in place. The arch wire 14A on the teeth 24 of the upper jaw is retained in a similar manner at its ends by a tube member 26 having an attached parallel tube section 28 which is utilized for retaining the inner end of an appliance member 12. Each tube member 26 with its attached head gear tube section 28 is welded to a band 29 on a rear molar 30 of the patient's upper jaw, with the ends 32 of the upper arch wire extending through the tube members 26.

Within each attached tube section 28, as shown best in FIG. 2, on the upper jaw is a slidable pin 34 having a length substantially greater that the tube section and a spherical ball 36 fixed to one end thereof. The other end of the pin 34 which extends from the other end of the tube section has a bent portion 38 extending away from its longitudinal axis to retain it within the tube section 28.

On the lower arch wire 14, for the embodiment of FIGS. 1 and 2, a swivel stop for the front end of each appliance member is also provided by a spherical ball 40 Preferably, this lower ball is retained in its desired position on the bottom portion of a U-shaped wire 42 whose legs 44 are attached to the lower arch wire. The U-shaped wire can be attached to the arch wire 14 without removing it from its attachment brackets 16 by means of a pair of connector pads 46. The ball stop 40 is crimped to the lower portion of the U-shaped wire 42 at any desired location thereon or can slide forward and push on legs 44.

The balls 36 and 40 thus serve as attachment end stops for the appliance members 12 and it is seen that their precise positions within a patient's mouth can be readily adjusted to enable the appliance members to provide just the desired amount of force.

A somewhat modified arrangement for attaching the lower front ends of the appliance elements 12 is shown in FIG. 4. Here, a spherical ball 40A for each element is attached directly on the lower arch wire 14, at the desired location, depending on the length of the element. Preferably, the arch wire 14 is removed temporarily by the orthodontist in this instance and a crimp 47 is formed in the arch wire, as shown in FIG. 4A. This provides a fixed stop for the ball 40A against which the mesial end of the appliance element can bear and swivel.

Each appliance element 12 is constructed from a combination of elements which provide its flexible, yet axial force transmitting characteristics. As shown in detail in the embodiment illustrated in FIGS. 5A and 5B, the appliance element 12 comprises a coiled wire 48 of uniform thickness (0.020 to 0.030 inches) having a multiplicity of identical coils that are evenly spaced apart (e.g., 0.020 to 0.030).

In situations where some increased stiffness with resiliency is desired, a modified element 12a may be used, as shown in FIG. 5C. Here, a central core 66 of a resilient, elastomeric or plastic material is provided within the length of the coiled wire 48. This core may be cylindrical, with a diameter that is sufficient to enable it to transmit an axial compression force from end to end along its centerline when in a straight configuration but sufficiently slender so that it will bend due to excessive axial force or due to side forces which may occur when a patient is chewing Thus, it enhances the flexibility and resiliency of the coiled wire. The coils at the ends of the coiled wire 48 also provide a means to connect them with a pair of end caps 50 and 52. Each end cap, which is currently formed from a rigid metal material, has a sleeve-like body 54 with internal threads 56 which thread with and provide a positive connection for retaining the coiled wire 48. Extending at an angle (e.g., 45°) from the body of each end cap is a rigid flange 58 having a flat face 60 and an opening 62 through the flange. As shown, the flanges for the end caps at opposite ends of the element 12 are angularly offset by a predetermined amount (e.g., 90°) so that, when installed, the flange faces will bear tangentially on the ball stops 36 and 40 at opposite ends without causing any twist in the element 12.

Surrounding the coiled wire is a flexible material 64 that provides a smooth outer surface that is essentially flush with the outer surface of each end cap body. This material, such as silicone rubber, may be formed by a molding process wherein the material flows in and around the wire coils thereby sealing the element 12 and providing improved hygiene and comfort.

Another modified element 12b, as shown in FIG. 5D. Here, the coiled wire is replaced by a solid, molded nonmetallic, flexible and cylindrical body 68 is connected to and extends between the end caps 50 and 52. This body member 68 may be molded in the desired length from a suitable resilient plastic material such as one made by the Celanese Corporation under the trademark Duralloy 1200. Such a material will provide the necessary strength, flexibility and resiliency to function as an appliance element in accordance with the invention. Also, the outer surface of the cylindrical body member, being flush with the element end caps provides the necessary hygienic comfort characteristics.

Although FIGS. 1 to 6 illustrate the present invention when installed in a patient's mouth having braces to correct an overbite condition, a modified appliance 10A can be used to correct an underbite condition wherein the patient's lower jaw extends abnormally outwardly from the upper jaw. Here, the teeth of the upper jaw tend to close inside the lower jaw teeth when the jaws are brought together. As shown in FIG. 7, this underbite condition is treated by essentially reversing the attachment locations or end stops on the upper and lower jaws so that the appliance 10A can be adjusted to provide a force that tends to push the lower jaw back from the upper jaw toward the normal bite position. Thus, in this instance, one end of the appliance element 12A is attached to the arch wire 14A on the upper teeth near a bicuspid tooth, using either a U-shaped member 42A with a ball stop 40 thereon and connected to the upper arch wire, as shown, or a similar ball stop attached directly on the arch wire having a stopping bend, as previously described. The other end of each appliance element 12A bears against a ball stop 36A on an adjustable pin 34A which extends through a sleeve section 28A anchored to a molar tooth on the patient. Again, the appliances 10A when properly adjusted, will apply the proper amount of corrective force to overcome the underbite condition, and, as with the overbite installation, the appliance element 12A will flex and swivel at their ends to allow the patient to talk, chew and move his jaws to facilitate teeth brushing and the like.

The present invention may also be utilized for patients who are not wearing braces, as shown in FIG. 8. Here, a suitable device that provides an anchoring means for the appliance elements must be used. As indicated, a pair of rigid plastic cover inserts 70 and 72 for both the upper and lower jaws are provided. Various configurations of cover inserts may be used, each being essentially a light plastic framework that fits over and is anchored to groups of teeth in the upper and lower jaws. Each cover framework may be formed to fit the patient's mouth and extend over whatever number of teeth are required to provide a firm anchor. For an overbite corrective appliance, the upper cover frame 70 may cover only the molar teeth. Attached to and anchored within each side of this cover frame is a sleeve 28B for retaining an adjustable pin 34B with a ball stop 36B fixed at its outer end, as previously described. The cover framework 72 on the lower jaw, also preferably molded from a strong but light plastic, preferably fits over a larger number of teeth and extends downwardly over their outer surfaces so as to provide an anchoring means for a U-shaped wire 42B having another ball stop 40B fixed thereon. Before the wire 42B is attached to the lower cover frame 72, one end of an appliance element 12B is attached to the wire 42B. When the lower cover frame 72 with two appliance elements 12B is installed in the patient's mouth, the inner ends of the elements can then be attached to the upper cover frame 70 by means of the slidable pins 34B in the same manner as previously described with respect to the embodiment using braces.

The installation of the appliance 10 for a patient with braces can be performed relatively easily by a skilled orthodontist in a small amount of time. With reference to FIG. 6, the lower, front end of the appliance element 12 is first attached either to a U-shaped wire extension 42 having a ball stop 40 as shown, or directly to the lower arch wire 14, as shown in FIG. 4. In either case, the U-shaped wire or arch wire extends through the opening 62 in an end cap flange of the appliance element 12. Now, the upper end of the appliance element can be attached to a sliding pin 34 before it is inserted into the molar tube or sleeve section 28. Again the pin passes through the opening in the angular end cap flange of the element 12 so the face of the flange bears against the ball stop 36 on the sliding pin. With the patient's mouth in the normal bite position, the proper axial corrective force to be exerted by each element 12 is adjusted by positioning the pin within its sleeve 28 and thus the position of the ball stop 36. Once the proper position is determined, the free end 38 of the pin is simply bent up to hold it in place. Now, when the patient's mouth is open, as shown in FIG. 6, for cleaning, talking or chewing, the appliance 10 has a considerable latitude for manipulation including swivel movement at its ends as well as the capability of bending to facilitate necessary jaw movement.

When the appliance 10 has been installed by an orthodontist in a patient with or without braces, it cannot be removed by the patient. Thus, its highly effective corrective treatment is operative for a large percentage of the time including those periods when the patient may be talking, chewing or cleaning his or her mouth. The combined flexibility and swivel connections for the flexible appliance elements 12 enable them to apply a relatively light but adequate push force on the lower jaw and yet allowing them to flex, bend and/or turn when it is necessary for the patient to chew, talk and clean. Thus, the corrective treatment for the appliance 10 can be more effective while increasing the comfort or tolerance level and cosmetic factors for the patient.

Although the appliance 10 has been described as being used with a pair of elements 12, there are instances where the orthodontist may successfully treat a patient using only one flexible element 12 installed in the manner described.

To those skilled in the art to which this invention relates, many changes in construction and widely differing embodiments and applications of the invention will suggest themselves without departing from the spirit and scope of the invention. The disclosures and the descriptions herein are purely illustrative and are not intended to be in any sense limiting.

What is claimed is:

1. An orthodontic appliance for treating an overbite condition in a patient whose upper row of teeth lies abnormally forward of the lower row of teeth in the patient's lower jaw, comprising:
    upper attachment means adapted to be secured to at least some of said upper row of teeth;
    lower attachment means adapted to be secured to said lower row of teeth;
    at least one flexible, nonstretching appliance element each extending between and attached by swivel means to said upper attachment means and to said lower attachment means and adapted to lie on one side of the patient's jaw, said flexible element having sufficient stiffness to exert a small axial pushing force from end to end when flexed, each said element having end means for bearing against a said attachment means while allowing the element to swivel relative to said attachment means;
    whereby said appliance element, when installed in a patient's mouth and in a slightly flexed condition, exerts a small pushing force on the patient's upper and lower jaws, the swivelability tending to correct said overbite condition, said element allowing the patient to move his jaws to talk, chew and cleanse both rows of teeth.

2. The orthodontic appliance as described in claim 1 wherein a pair of said flexible appliance elements are provided and connected to said upper and lower attachment means, and when installed, lie on opposite sides of the patient's jaws.

3. The orthodontic appliance as described in claim 2 including an upper plastic member which is adapted to fit over and be anchored to at least some of the upper row of teeth and a lower plastic member adapted to be anchored to and extend over the lower row of teeth for a patient without braces, said upper attachment means being attached to said upper plastic member and said lower attachment being attached to said lower plastic member.

4. The orthodontic appliance as described in claim 3 wherein said upper attachment means comprises a tube, a movable pin partly in said tube and upper stop means comprising a spherical ball fixed on one end of said pin; and said lower attachment means comprises a fixed U-shaped wire having a lower stop means comprising a spherical ball thereon.

5. The orthodontic appliance as described in claim 2 wherein each said flexible appliance element comprises a resiliently flexible coiled wire end cap means fixed to each end of said coiled wire, each end cap having a flange portion which extends therefrom at an angle relative to the longitudinal axis of said appliance element.

6. The orthodontic appliance as described in claim 5 wherein said coiled wire is surrounded by a layer of flexible non-metallic material which extends between the coils of the wire and provides a smooth exterior surface on the appliance element.

7. The orthodontic appliance as described in claim 5 including a central core of resilient plastic material within said coiled wire and extending between said end caps to provide additional resiliency to each appliance element, and a flexible exterior layer surrounding said coiled wire.

8. The orthodontic appliance as described in claim 7 wherein said flexible exterior layer is silicone rubber.

9. The orthodontic appliance as described in claim 1, wherein said upper attachment means for each side of the patient's mouth includes a tube adapted to be anchored to at least one of said upper row teeth, a movable pin partly within and extending out from said tube, having upper stop means comprising a spherical ball fixed adjacent to its distal end and means at its other end for retaining said pin within said tube; said lower attachment means includes a fixed wire adapted to be anchored to at least some of said lower row of teeth and lower stop means comprising a spherical ball on said wire; and said end means of said flexible appliance element respectively are retained by and slide on said movable pin and said fixed wire and including a portion adapted to bear against said spherical ball stop means when the patient's lower jaw is held in the abnormal bite position.

10. The orthodontic appliance as described in claim 9 wherein said tube for said upper attachment means is adjacent a tube and is adapted to retain an arch wire on a patient's upper row of teeth.

11. The orthodontic appliance as described in claim 9 wherein said fixed wire for said lower attachment means is an arch wire for braces adapted to be used on said lower row of teeth, said arch wire having a bend for retaining said lower stop means.

12. The orthodontic appliance as described in claim 9 wherein each said fixed wire for said lower attachment means comprises a U-shaped wire section fixed to and extending below an arch wire for braces adapted to be used on said lower row of teeth.

13. An elongated force transmitting but flexible link element for use as an orthodontic appliance for counteracting an abnormal bite condition between a patient's upper and lower rows of teeth by producing a pushing force when flexed, said link element comprising:
    a non-stretching coiled wire having coils of uniform size and spaced apart along the length thereof;

a pair of end caps attached to opposite ends of said coiled wire, each said end cap having means for pivotally connecting said link element with attachment means that are adapted to be on the patient's upper and lower rows of teeth; and an outer layer of flexible material covering said coiled wire between said end caps.

14. The orthodontic appliance link element as described in claim 13 wherein each of said end cap has a tubular portion with internal threads for receiving said coiled wire at the end of said coiled wire.

15. The orthodontic appliance link element as described in claim 13 wherein each said end cap has a tubular portion for receiving one end of said coiled wire and an integral flange extending from said tubular portion at an angle of around 45° relative to the longitudinal axis of said tubular portion.

16. The orthodontic appliance link element as described in claim 13 wherein said outer layer of flexible material is silicone rubber.

17. The orthodontic appliance link element as described in claim 13 including a central core member extending between said end caps within said coiled wire, said core member being a flexible, resilient plastic member.

18. An orthodontic appliance for treating an underbite condition in a patient whose upper row of teeth lies abnormally rearward of the lower row of teeth in the patient's lower jaw, comprising:

fixed upper attachment means adapted to be secured to at least some of said upper row of teeth;

adjustable lower attachment means adapted to be secured to said lower row of teeth;

a pair of non-stretching flexible appliance elements extending between and attached by swivel means to said upper attachment means and said lower attachment means and adapted to lie on one side of the patient's jaw, said elements having sufficient stiffness to exert a small axial pushing force from end to end when flexed, said elements having end means for bearing against a said attachment means while allowing the elements to swivel relative to said attachment means:

whereby said appliance elements, when installed and in a slightly flexed condition, exert a small pushing force on the patient's upper and lower jaws, said elements being swivelable at their ends to allow movement thereof so that the patient can move his jaws to talk, chew and cleanse both rows of teeth.

19. The orthodontic appliance as described in claim 18 wherein each side of said lower attachment means includes a tube anchored to at least one of said lower row of teeth, a movable pin partly within and extending out from said tube having lower spherical stop means fixed to one end and means at its other end for retaining said pin within said tube; said upper attachment means including a fixed wire anchored to at least some of said lower row of teeth and upper spherical stop means on said wire; said flexible appliance including said end means being retained on said movable pin and said fixed wire and adapted to bear against and swivel around said spherical stop means when the patient's lower jaw is held in the abnormal underbite position.

20. An orthodontic appliance for treating malocclusion comprising:

upper attachment means adapted to be secured to at least some of the upper row of teeth;

lower attachment means adapted to be secured to at least some of the lower row of teeth;

at least one non-stretching flexible appliance element extending between said upper attachment means and adapted to lie on one side of the patient's jaw, said element when flexed exerting a small axial pushing force to each said attachment means, said element having a swivel connection to each said attachment means;

whereby said appliance element, when installed in a patient's mouth and in a slightly flexed condition, exerts a small pushing force on the patient's upper and lower jaws while swiveling at its ends to allow the patient to move his jaws in order to talk, to chew, and to cleanse both rows of teeth.

* * * * *